United States Patent [19]

Lenhard et al.

[11] 4,147,801

[45] Apr. 3, 1979

[54] COMPLEMENT INHIBITORS

[75] Inventors: Robert H. Lenhard, Paramus, N.J.; Seymour Bernstein, New City, N.Y.

[73] Assignee: American Cyanamid Company, Stamford, Conn.

[21] Appl. No.: 875,704

[22] Filed: Feb. 6, 1978

Related U.S. Application Data

[62] Division of Ser. No. 684,599, May 10, 1976, Pat. No. 4,087,548.

[51] Int. Cl.$^2$ ............................................. A61K 31/185
[52] U.S. Cl. .................................... 424/315; 260/506; 260/507 R; 424/12
[58] Field of Search ............. 424/315; 260/506, 507 R

[56] References Cited

U.S. PATENT DOCUMENTS

| | | | |
|---|---|---|---|
| 3,897,434 | 7/1975 | Katner | 260/256.4 Q |
| 3,903,106 | 9/1975 | Katner | 260/310 R |
| 4,027,038 | 5/1977 | Bernstein | 424/315 |
| 4,046,805 | 9/1977 | Bernstein | 424/315 X |
| 4,051,176 | 9/1977 | Lenhard | 424/315 X |
| 4,087,548 | 5/1978 | Lenhard | 424/315 |

OTHER PUBLICATIONS

Fourneau, Ann Inst. Pasteur, vol. 38, 1924, pp. 81–114.
Adams, J. Chem. Soc. (London) Part III, 1956, pp. 3739–3744.
Wills, The Biochem. J., vol. 47, 1950, pp. 158–170.
Fong, Clin. Exp. Immunol., vol. 10, 1972, pp. 127–138.
Mayer, Sci. Amer., vol. 229, Nov. 1973, pp. 54–66.
Bergamini, Chem. Abs., vol. 43, 1949, p. 3855ghi.
Jose, Chem. Abs., vol. 71, 1969, Ab. No. 20472z.
Balaban, J. Chem. Soc. (London) 1927, pp. 3068–3097.

*Primary Examiner*—Anna P. Fagelson
*Attorney, Agent, or Firm*—Jack W. Richards

[57] ABSTRACT

Certain C-substituted trisulfonic acids, acid ureides, oxalyl amides and salts thereof useful as complement inhibitors.

7 Claims, No Drawings

COMPLEMENT INHIBITORS

This is a division, of application Ser. No. 684,599, filed May 10, 1976, now U.S. Pat. No. 4,087,548.

BACKGROUND OF THE INVENTION

The present invention resides in the concept of certain C-substituted trisulfonic acids, acid ureides and oxalyl amides, such as the C1-substituted or C2-substituted, 1,3,6-trisulfonic acids, acid ureides and oxalyl amides, and salts thereof; and their use as inhibitors of the complement system of warm-blooded animals.

The term "complement" refers to a complex group of proteins in body fluids that, working together with antibodies or other factors, play an important role as mediators of immune, allergic, immunochemical and/or immunopathological reactions. The reactions in which complement participates takes place in blood serum or in other body fluids and hence are considered to be humeral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in body processes can be found in, for example, *Bull. World Health Org.*, 39, 925–938 (1968); *Scientific American*, 229, (No. 5), 54–66 (1973); *Medical World News*, Oct. 11, 1974, pp. 53–58; 64–66; *Harvey Lectures*, 66, 75–104 (1972); *The New England Journal of Medicine*, 287, 489–495; 545–549; 592–596; 642–646 (1972); *The Johns Hopkins Med. J.*, 128, 57–74 (1971); and *Federation Proceedings*, 32, 134–137 (1973).

The complement system can be considered to consist of three sub-systems: (1) a recognition unit (C1q) which enables it to combine with antibody molecules that have detected a foreign invader; (2) an activation unit (C1r, C1s, C2, C4, C3), which prepares a site on the neighboring membrane; and, (3) an attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is therefore a double edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxic sometimes results in serum sickness, an immune-complex disease. Rheumatoid arthritis also involves immune complexes. Like disseminated lupus srythematosus, it is autoimmune disease, in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection, it also results in inflammation and tissue damage in the immunopathological process. The nature of certain of the complement proteins, suggestions regarding the mode of complement binding to biological membranes and the manner in which complement effects membrane damage are discussed in *Annual Review of Biochemistry*, 38, 389 (1969).

A variety of substances have been disclosed as inhibiting the complement system, i.e., as complement inhibitors. For example, the compounds 3,3'-ureylenebis[6-(2-amino-8-hydroxy-6-sulfo-1-naphthylazo)benzenesulfonic acid], tetrasodium salt (chlorazol fast pink), heparin and a sulphated dextran have been reported to have an anticomplementary effect, *British Journal of Experimental Pathology*, 33, 327–339 (1952). The compound 8,8'-[ureylenebis[m-phenylcarbonylimino(4-methyl-m-phenylene)carbonylimino]]di-1,3,5-naphthalenetrisulfonic acid, hexasodium salt (Suramin Sodium) is described as a competitive inhibitor of the complement system, *Clin. Exp. Immunol.*, 10, 127–138 (1972). German Pat. No. 2,254,893 or South African Pat. No. 727,923 discloses certain 1-(diphenylmethyl)-4-(3-phenylallyl)piperazines useful as complement inhibitors. U.S. Pat. No. 3,897,434 discloses certain pyrazolo[1,5-c]quinazolin-5(6H)-ones and U.S. Pat. No. 3,903,106 certain pyrazolo-3-carboxylic acids, both groups of compounds useful as complement inhibitors. The compound, m-[m-(p-nitrophenylureido)phenoxypropoxy]benzamidine is also known as a complement inhibitor, *Immunology*, 26, 819 (1974). Other chemical compounds having complement inhibiting activity are disclosed in, for example, *Journal of Medicinal Chemistry*, 12, 415–419; 902–905; 1049–1052; 1053–1056 (1969); *Canadian Journal of Biochemistry*, 47, 547–552 (1969); *The Journal of Immunology*, 93, 629–640 (1964); *The Journal of Immunology*, 104, 279–288 (1970); *The Journal of Immunology*, 106, 241–245 (1971); and *The Journal of Immunology*, 111, 1061–1066 (1973).

It has been reported that the known complement inhibitors epsilon-aminocaproic acid, Suramin Sodium and tranexamic acid have been used with success in the treatment of hereditary angioneurotic edema, a disease state resulting from an inherited deficiency or lack of function of the serum inhibitor of the activated first component of complement (C1-inhibitor), *The New England Journal of Medicine*, 286, 808–812 (1972); *Allergol, Et. Immunopath*, II, 163–168 (1974); and *J. Allergy Clin. Immunol.*, 53, No. 5, 298–302 (1974).

SUMMARY OF THE INVENTION

It has now been discovered that compounds of the invention interact with the complement reaction sequence, thereby inhibiting complement activity in body fluid.

Broadly, this invention is concerned with the use of C-substituted trisulfonic acids, acid ureides, oxalyl amides and salts thereof which can be represented by general formula (I):

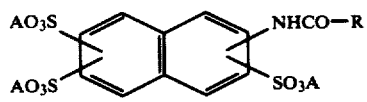
(I)

wherein R is 

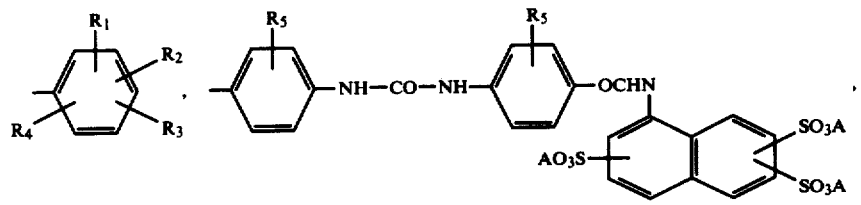

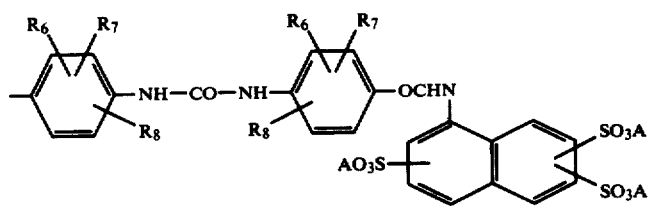

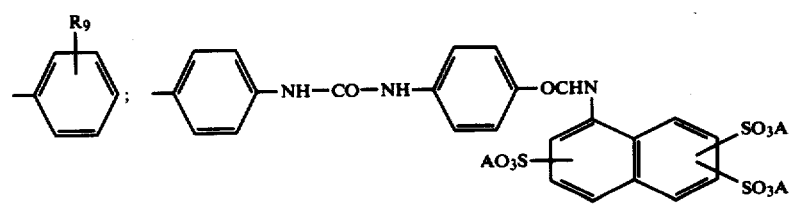

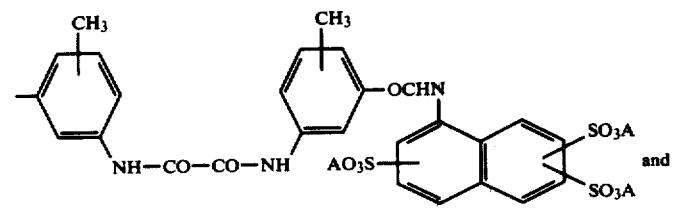

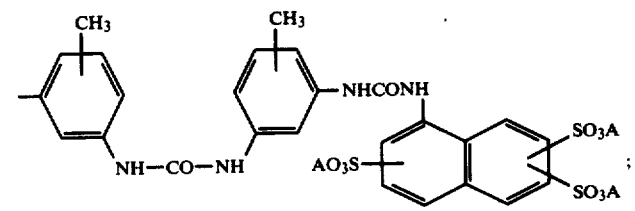

$R_1$, $R_2$, $R_5$, $R_6$, $R_7$, and $R_8$ are hydrogen or methyl; $R_3$ and $R_4$ are hydrogen, methyl, amino, nitro, $R_9$ is amino or nitro; and A is hydrogen, alkali metal and alkaline earth, with the proviso that each A is identical in the same compound. Preferably, A is sodium and potassium.

Of the compounds encompassed within general formula (I), those of most interest are those represented by general formula (II):

(II)
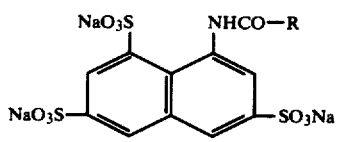
wherein R is ,
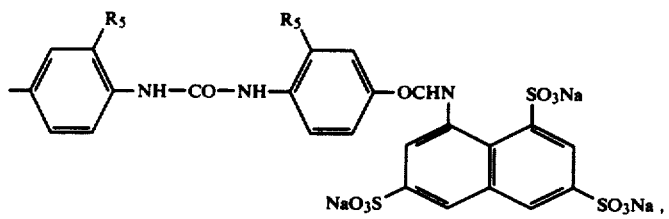
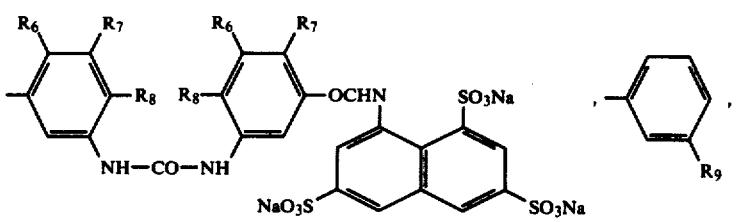
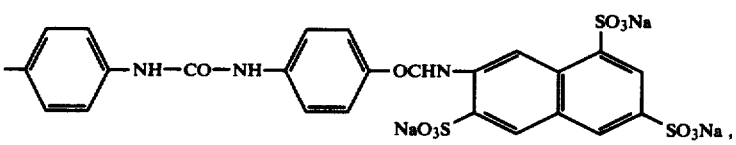
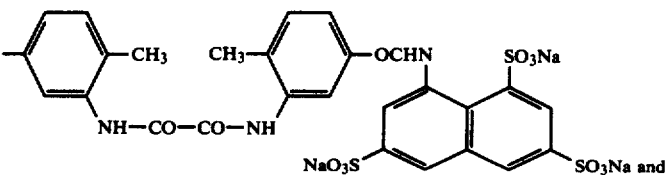
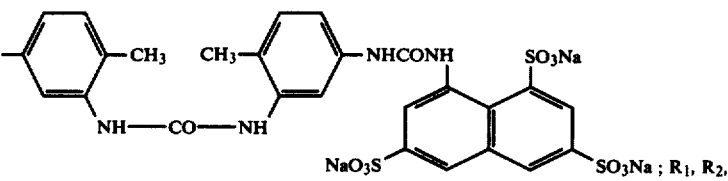
$R_5$, $R_6$, $R_7$ and $R_8$ are hydrogen or methyl; $R_3$ and $R_4$ are hydrogen, methyl, amino, nitro,
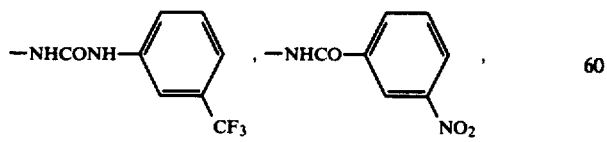,
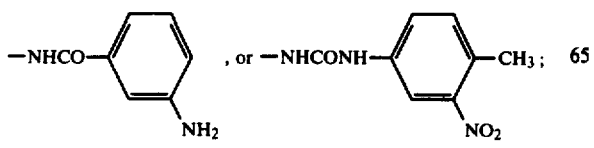;
and $R_9$ is amino or nitro.
Of the compounds encompassed with general formula (I) and (II), those of most interest are the C8-substituted 1,3,6-trisulfonic acid salts of formula (III):

(III)

wherein $R_1$ and $R_2$ are selected from the group comprising hydrogen and methyl and $R_3$ and $R_4$ are selected from the group comprising hydrogen, methyl, amino, nitro,

certain C8-substituted acid ureide salts of formula (IV):

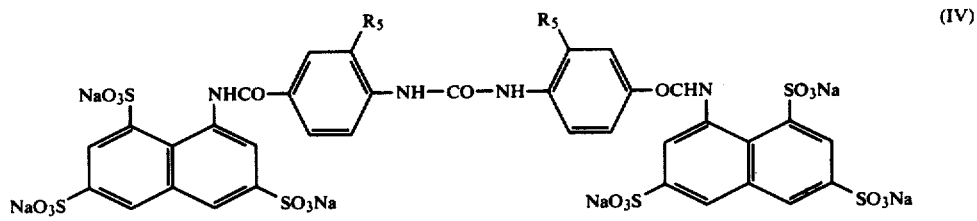

wherein $R_5$ is selected from the group comprising hydrogen and methyl; compounds of formula (V):

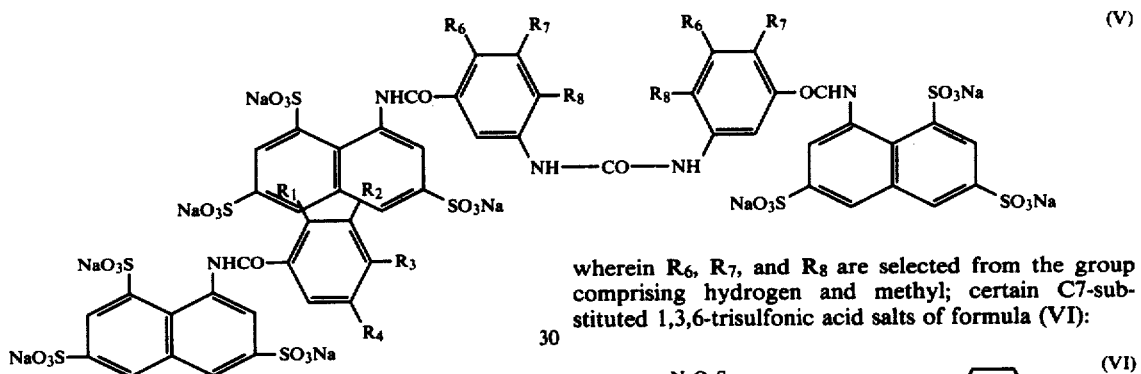

wherein $R_6$, $R_7$, and $R_8$ are selected from the group comprising hydrogen and methyl; certain C7-substituted 1,3,6-trisulfonic acid salts of formula (VI):

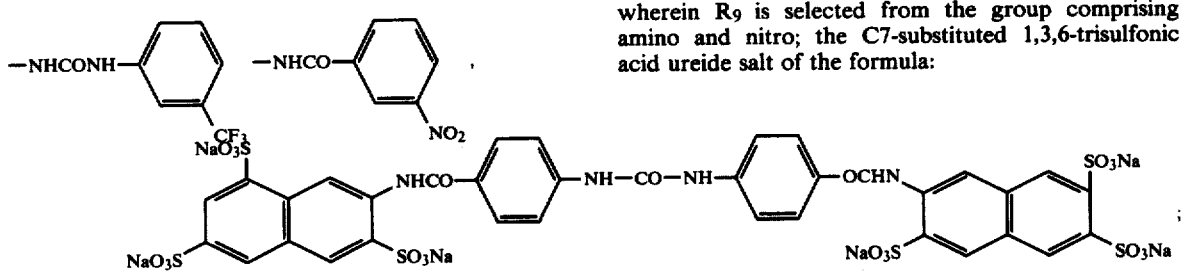

wherein $R_9$ is selected from the group comprising amino and nitro; the C7-substituted 1,3,6-trisulfonic acid ureide salt of the formula:

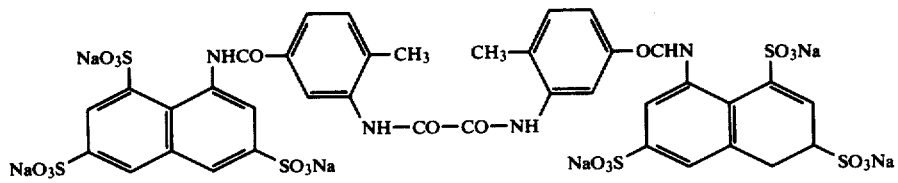

the C8-substituted 1,3,6-trisulfonic acid oxalyl amide salt of the formula:

and the 1,3,6-trisulfonic acid ureide of the formula:

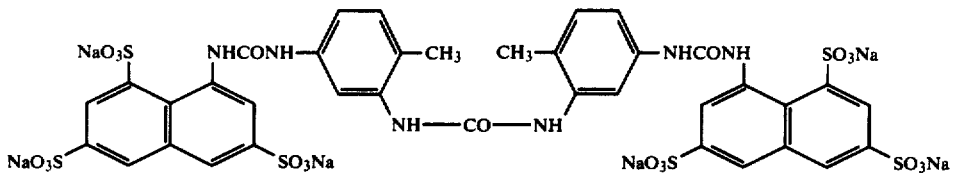

The following references disclose compounds falling within the method of this invention: *J. Chem. Soc.*, 3739 (1956); *Biochem. J.*, 47, 158 (1950); and *Ann. Inst. Pasteur*, 38, 81 (1924).

This invention is particularly concerned with the use of the following specific compounds. 8-p-Nitrobenzamido-1,3,6-naphthalenetrisulfonic acid, trisodium salt; 8-(p-Aminobenzamido)-1,3,6-naphthalenetrisulfonic acid, trisodium salt; 8-{p-[3-($\alpha,\alpha,\alpha$-Trifluoro-m-tolyl)ureido]benzamido}-1,3,6-naphthalenetrisulfonic acid, trisodium salt; 8-(4-Nitro-m-toluamido)-1,3,6-naphthalenetrisulfonic acid, trisodium salt; 8-(4-Amino-m-toluamido)-1,3,6-naphthalenetrisulfonic acid, trisodium salt; 8-m-Nitrobenzamido-1,3,6-naphthalenetrisulfonic acid, trisodium salt; 8-(m-Aminobenzamido)-1,3,6-naphthalenetrisulfonic acid, trisodium salt; 8-[m-(m-Nitrobenzamido)benzamido]-1,3,6-naphthalenetrisulfonic acid, trisodium salt; 8-[m-(m-Aminobenzamido)benzamido]-1,3,6-naphthalenetrisulfonic acid, trisodium salt; 8-{m-[3-(3-Nitro-p-tolyl)ureido]benzamido}-1,3,6-naphthalenetrisulfonic acid, trisodium salt; 8-(3-Nitro-p-toluamido)-1,3,6-naphthalenetrisulfonic acid, trisodium salt; 8-(3-Amino-p-toluamido)-1,3,6-naphthalenetrisulfonic acid, trisodium salt; 8-{3-[3-(3-Nitro-p-tolyl)ureido]-p-toluamido}-1,3,6-naphthalenetrisulfonic acid, trisodium salt; 8-(5-Nitro-o-toluamido)-1,3,6-naphthalenetrisulfonic acid, trisodium salt; 8-(5-Amino-o-toluamido)-1,3,6-naphthalenetrisulfonic acid, trisodium salt; 8,8'-[Ureylenebis(p-phenylenecarbonylimino)]di-1,3,6-naphthalenetrisulfonic acid, hexasodium salt; 8,8'-[Ureylenebis(3-methyl-p-phenylenecarbonylimino)]di-1,3,6-naphthalenetrisulfonic acid, hexasodium salt; 8,8'-[Ureylenebis(m-phenylenecarbonylimino)]-di-1,3,6-naphthalenetrisulfonic acid, hexasodium salt; 8,8'-[Ureylenebis(4-methyl-m-phenylenecarbonylimino)]di-1,3,6-naphthalenetrisulfonic acid, hexasodium salt; 8,8'-[Ureylenebis(6-methyl-m-phenylenecarbonylimino)]di-1,3,6-naphthalenetrisulfonic acid, hexasodium salt; 7-m-Nitrobenzamido-1,3,6-naphthalenetrisulfonic acid, trisodium salt; 7-(m-Aminobenzamido)-1,3,6-naphthalenetrisulfonic acid, trisodium salt; 7,7'-[Ureylenebis(m-phenylenecarbonylimino)]di-1,3,6-naphthalenetrisulfonic acid, hexasodium salt; 8,8'-{Oxalylbis{[imino(4-methyl-1,3-phenylene)]carbonyl}imino}}di-1,3,6-naphthalenetrisulfonic acid, hexasodium salt; and 8,8-{Ureylenebis[(4-methyl-m-phenylene)ureylene]}di-1,3,6-naphthalenetrisulfonic acid, hexasodium salt.

The compounds of formulae I–VI are either known compounds whose preparation is described in the chemical literature or may be obtained by the application of known methods. Representative compounds of this invention may be prepared as shown by the examples herein and according to the exemplary methods described below. The compounds of the present invention may be prepared by acylation of the respective naphthylaminetrisulfonic acid with m-nitrobenzoyl chloride followed by catalytic reduction and subsequent condensation of the respective amine with the appropriate substituted phenylisocyanate; or by phosgenation of the respective amine. Acidification produces the free acid. A more explicit illustration of the reaction follows:

Schotten-Baumann acylation

To a solution of the sodium salt of a naphthylaminetrisulfonic acid in an appropriate amount of water and 1N sodium hydroxide is added m-nitrobenzoyl chloride. The mixture is shaken until no longer basic to test paper. Three additional equal portions of 1N sodium hydroxide are added, shaking between each addition until the solution is no longer basic. After the last portion of base is added, the reaction mixture is shaken for at least 30 minutes and then the still basic solution is acidified to Congo Red with concentrated hydrochloric acid. The reaction mixture is then copiously extracted with ether to remove the m-nitrobenzoic acid side product (by vacuum siphoning of the ethereal layer). The aqueous phase is then filtered to remove a small amount of the anhydride of m-nitrobenzoic acid and the filtrate is concentrated in vacuo at 50°–60° C. until a solid is precipitated. After cooling to ambient temperature, the product is filtered and is washed with saturated saline solution, 50% ethyl alcohol, absolute ethyl alcohol and ether.

Catalytic reduction

Treatment of a solution of the appropriate amount of the desired m-nitrobenzamide of naphthalenetrisulfonic acid in 160–200 ml of water with 1.0–3.7 g of 10% palladium on carbon in a Parr apparatus under an initial hydrogen pressure of 42 pounds per square inch gives a theoretical uptake of hydrogen in 1¾ hours. The reaction mixture is filtered through diatomaceous earth and the catalyst is washed with water. The filtrate is concentrated under reduced pressure at 50°–60° C. to low volume and is then diluted with a large volume of absolute ethanol. The precipitated product is collected and is washed with absolute ethyl alcohol.

Phosgenation

Phosgene is bubbled through a mechanically stirred solution of the desired aminobenzamide of naphthalenetrisulfonic acid in the appropriate amount of water containing a theoretical quantity of sodium carbonate until the reaction mixture becomes acidic to Congo Red. An additional quantity of carbonate is cautiously added and the process is repeated ntil the reaction mixture is again acidic. It is then neutralized with bicarbonate and is concentrated in vacuo at 50°–60° C. On cooling to room temperature a solid is formed which is filtered and is washed with 80% ethyl alcohol, absolute ethyl alcohol and ether.

Acylation with isocyanates

A solution of the appropriate amount of the desired m-aminobenzamide of naphthalenetrisulfonic acid sodium salt in water is treated with a theoretical portion of the required isocyanate and is stirred vigorously for 6 hours at room temperature. The reaction mixture is diluted with additional water, is heated to approximately 95° C. for 30 minutes and is filtered through diatomaceous earth and is washed with hot water. The filtrate is treated with sodium chloride while heating on the steam bath and is allowed to stand at room temperature overnight (lower temperature is required in some cases). The precipitate is collected and is boiled with absolute ethyl alcohol then is allowed to stand at room temperature for several days. The product is then filtered and washed with absolute ethyl alcohol and ether.

In the use of the aforementioned compounds, this invention is concerned with a method of inhibiting the complement system in a body fluid, such as blood serum, which comprises subjecting body fluid complement to the action of an effective complement inhibiting amount of a compound encompassed within the formulae hereinabove. The method of use of this invention is also concerned with a method of inhibiting the complement system in a warm-blooded animal which comprises internally administering to said animal an effective complement inhibiting amount of a compound encomassed within the formulae hereinabove. Body fluid can include blood, plasma, serum, synovial fluid, cerebrospinal fluid, or pathological accumulations of fluid as pleural effusion, etc.

The compounds of the present invention find utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of auto-allergic hemolytic anemia, certain kinds of platelet disorders and certain kinds of vasculitis. The compounds herein may also be used in the therapeutic treatment of warm-blooded animals having non-immunologic diseases such as paroxysmal diseases such as paroxysmal nocturnal hemoglobinuria, hereditary angioneurotic edema (treated with Suramin, etc.) and inflammatory state induced by the action of bacterial or lysosomal enzymes on the appropriate complement components as for example, inflammation following coronary occlusion. They may also be useful in the treatment of transplant rejection and as a blood culture or transport mediums.

DETAILED DESCRIPTION OF THE INVENTION

The following examples describe in detail the preparation and formulation of representative compounds of the present invention.

EXAMPLE 1

7-m-Nitrobenzamido-1,3,6-naphthalenetrisulfonic acid, trisodium salt

A 224 g portion of 7-amino-1,3,6-naphthalenetrisulfonic acid, disodium salt (DuPont) is triturated in 600 ml of methanol at room temperature, filtered and washed with methanol and ether.

A 51.3 g portion of this disodium salt is combined with 120 ml of 1N NaOH, 60 ml of water and 45 g of m-nitrobenzoylchloride. The reaction mixture sets up to an unshakable sludge. A 120 ml portion of 1N NaOH and 60 ml of water are added and the mixture is shaken for 10-15 minutes. At intervals three more 120 ml portions of 1N NaOH are added and the mixture is shaken for a total of 2 hours. The mixture is diluted with several hundred ml of water until clear and acidified with 22 ml of concentrated HCl. The mixture is extracted with six 150 ml portions of ether by syphoning off the extracts. The aqueous phase becomes turbid and is neutralized with NaOH. After standing overnight at room temperature the mixture is filtered. The filtrate is concentrated in vacuo at 65° C. until crystals appear. The filtrate, after standing overnight is washed twice with 100 ml of saturated saline, twice with 100 ml of 50% ethanol, twice with 100 ml of absolute alcohol and finally twice with 150 ml of ether giving 40.4 g of product.

EXAMPLE 2

8-m-Nitrobenzamido-1,3,6-naphthalenetrisulfonic acid, trisodium salt

The procedure of Example 1 is repeated using 53.9 g of 8-amino-1,3,6-naphthalenetrisulfonic acid, trisodium salt (Eastman). A total of 480 ml of 1N NaOH is used. The mixture is acidified with 15 ml of concentrated HCl and extracted copiously with ether. The aqueous phase is filtered through sintered glass and the filtrate is neutralized. The filtrate is concentrated in vacuo at 55°-60° C. to ½ volume, forming a solid. A 200 ml portion of saturated saline and 100 ml of water is added and the mixture is triturated, filtered and washed with 200 ml of saturated saline, two 300 ml portions of 90% ethanol, 400 ml of absolute alcohol and two 300 ml portions of ether giving 71.8 g of product.

EXAMPLE 3

8-(m-Aminobenzamido)-1,3,6-naphthalenetrisulfonic acid, trisodium salt

A 50.0 g portion of the product prepared as described in Example 2 in 210 ml of water containing 4.0 g of 10% palladium on carbon catalyst is hydrogenated at room temperature and an initial pressure of 42 pounds for 4¾ hours. The mixture is filtered. The filtrate is evaporated in vacuo at 55°-60° C. to a low volume, diluted with absolute alcohol, filtered and washed with absolute alcohol, giving 43.06 g of product.

EXAMPLE 4

7-(m-Aminobenzamido)-1,3,6-naphthalenetrisulfonic acid, trisodium salt

A 25.0 g portion of the product prepared as described in Example 1 in 200 ml of water containing 2.0 g of 10% palladium on carbon catalyst is hydrogenated and treated as described in Example 3 for 2¼ hours giving 23.03 g of product.

EXAMPLE 5

8,8'-[Ureylenebis(m-phenylenecarbonylimino)]di-1,3,6-naphthalenetrisulfonic acid, hexasodium salt A solution of 10.0 g of 8-(m-aminobenzamido)-1,3,6-naphthalenetrisulfonic acid, trisodium salt in 250 ml of water containing 3.75 g of anhydrous sodium carbonate is prepared. Phosgene is bubbled through a sintered glass diffuser into this stirred solution at a slow to moderate rate for one hour. A 3.75 g portion of sodium carbonate in 10-15 ml of water is added, followed by two 3.75 g portions of solid sodium carbonate. Phosgenation is continued until the mixture is acidic to Congo Red. Another 3.75 g portion of sodium carbonate is added and phosgenation is continued for 15 minutes. The acidic mixture is neutralized with 2.1 g of sodium carbonate and concentrated in vacuo at 55°-60° C. to a low volume. Sodium chloride precipitates and is removed by filtration. A second precipitate is removed by filtration and washed with methanol. The combined filtrate and washings, on standing deposit a third precipitate which is redissolved by heating on a steam bath, filtered hot and the filtrate is cooled overnight at 0°–5° C. The 6.1 g of product is recovered by filtration and washing with ice-cold methanol.

EXAMPLE 6

7,7'-[Ureylenebis(m-phenylenecarbonylimino)]di-1,3,6-naphthalenetrisulfonic acid, hexasodium salt A solution of 10.0 g of 7-(m-aminobenzamido)-1,3,6-naphthalenetrisulfonic acid, trisodium salt in 250 ml of water containing 15 g of anhydrous sodium bicarbonate is prepared. Phosgene is bubbled through this solution with stirring at room temperature for 90 minutes. Four 3.75 g portions of solid sodium carbonate are added. Phosgene is bubbled through the solution for 15 minutes. A 6 g portion of solid sodium carbonate is added and the mixture gradually thickens to a gel which is filtered and washed with 80% ethanol. The moist solid is washed through the filter with 60 ml of boiling water and neutralized. The filtrate is concentrated in vacuo to a syrup and an amorphous mass which is then dissolved in 20 ml of hot water, diluted with 80 ml of absolute alcohol and 100 ml of 80% ethanol and allowed to stand at room temperature for 90 minutes. The mixture is filtered and washed with 80% ethanol. This solid is boiled with 200 ml of absolute methanol and filtered, giving 6.83 g of product.

EXAMPLE 7

8-[m-(m-Nitrobenzamido)benzamido]-1,3,6naphthalene-trisulfonic acid, trisodium salt A 25.0 g portion of 8-(m-aminobenzamido)-1,3,6-naphthalenetrisulfonic acid, trisodium salt, 45 ml of 1N NaOH, 30 ml of water and 16.5 g of m-nitrobenzoyl chloride are combined and shaken. Three additional 45 ml portions of 1N NaOH are added with shaking after each portion. The mixture is acidified with 10 ml of concentrated HCl and extracted with seven 150 ml portions of ether. The ether extracts are syphoned off and 200 ml of water is added to solubilize the product. The aqueous phase is neutralized and concentrated in vacuo at 50°–55° C. until a solid precipitates. After standing overnight at room temperature the mixture is filtered and the solid is washed with 200 ml of saturated saline. The moist paste is dissolved in 50 ml of hot water and diluted with 250 ml of hot absolute alcohol, resulting in a thick paste. The paste is diluted with 100 ml of 80% ethanol and filtered. The solid is slurried on the funnel with 250 ml of absolute alcohol and then filtered giving 25.48 g of product.

EXAMPLE 8

8-[m-(m-Aminobenzamido)benzamido]-1,3,6-naphthalene-trisulfonic acid, trisodium salt A 20.0 g portion of the product prepared as described in Example 7 in 160 ml of water containing 2.0 g of 10% palladium on carbon catalyst is hydrogenated at room temperature and 44 pounds pressure for 3 hours. The catalyst is filtered off and the filtrate is evaporated to near dryness at 50°–55° C. The resulting oil is diluted with absolute alcohol, triturated, filtered and washed with absolute alcohol giving 17.84 g of product.

EXAMPLE 9

8-p-Nitrobenzamido-1,3,6-naphthalenetrisulfonic acid, trisodium salt

A 5.39 g portion of 8-amino-1,3,6-naphthalenetrisulfonic acid, trisodium salt (Eastman), 20 ml of water, 12 ml of 1N NaOH and 4.5 g of p-nitrobenzoyl chloride are shaken together. The procedure of Example 7 is followed. A total of 48 ml of 1N NaOH is used. Ether extraction results in crystals which are dissolved in water and 80% ethanol and evaporated to a low volume. These crystals are filtered and washed with absolute alcohol giving 6.01 g of product.

EXAMPLE 10

8-(p-Aminobenzamido)-1,3,6-naphthalenetrisulfonic acid, trisodium salt

A 25.0 g portion of the product prepared as described in Example 9 in 100 ml of water containing 2.5 g of 10% palladium on carbon catalyst is hydrogenated at room temperature and an initial pressure of 46 pounds for 2 hours and 41 minutes. The catalyst is filtered off. The filtrate is concentrated in vacuo at 55°–60° C. to a low volume producing crystals. These crystals are triturated in 300 ml of absolute alcohol, filtered and washed with absolute alcohol giving 21.8 g of product.

EXAMPLE 11

8,8'-[Ureylenebis(p-phenylenecarbonylimino)]di-1,3,6-naphthalenetrisulfonic acid, hexasodium salt A mixture of 10.0 g of the product prepared as described in Example 10, 250 ml of water and 18.6 g of anhydrous sodium carbonate is phosgenated for 33 minutes. An additional 18.6 g of sodium carbonate is added and the mixture is phosgenated for one hour. The mixture is neutralized with 5N NaOH, concentrated in vacuo at 50°–55° C. to about 200 ml and cooled to room temperature giving a precipitate which is filtered and washed with two 100 ml portions of 90% ethanol and then two 125 ml portions of absolute ethanol. This solid is slurried in 200 ml of boiling absolute methanol, cooled to room temperature, filtered and washed with cold methanol giving 10.2 g of product.

EXAMPLE 12

8,8'-{Ureylenebis[(4-methyl-m-phenylene)ureylene]}di-1,3,6-naphthalenetrisulfonic acid, hexasodium salt A 15.0 g portion of 8-amino-1,3,6-naphthalenetrisulfonic acid, trisodium salt in 200 ml of water containing 15.0 g of p-methyl-m-nitrophenyl isocyanate is stirred vigorously for 6 hours and then heated to 85°–90° C. for 30 minutes. The mixture is then filtered and washed with water. The filtrate is salted with 125 g of sodium acetate trihydrate with warming and filtered after standing at room temperature overnight. The solid is washed copiously with absolute alcohol and ether giving 9.73 g of 8-[3-(3-nitro-p-tolyl)ureido]naphthalene-1,3,6-trisulfonic acid sodium salt.

A 9.73 g portion of the above product in 100 ml of water containing 1.0 g of 10% palladium on carbon catalyst is hydrogenated at room temperature and a pressure of 47 pounds for 4 hours. The catalyst is filtered off. The filtrate is evaporated to dryness and slurried with absolute alcohol. The slurry is filtered and washed with absolute alcohol giving 8.89 g of the corresponding amino derivative.

An 8.89 g portion of this amino derivative in 225 ml of water containing 15.8 g of anhydrous sodium carbonate is phosgenated as described in Example 5 using a total of 52.4 g of sodium carbonate. Neutralization and concentration in vacuo at 50°–55° C. produces a solid precipitate. This solid is filtered and washed with absolute alcohol and then dissolved in 40 ml of hot water. The filtrate is diluted with 240 ml of absolute alcohol with heat. Cooling, filtration and washing with absolute alcohol produces 7.69 g of the final product.

EXAMPLE 13

8-(3-Nitro-p-toluamido)-1,3,6-naphthalenetrisulfonic acid, trisodium salt

A 25.6 g portion of 8-amino-1,3,6-naphthalenetrisulfonic acid, trisodium salt in 100 ml of water and 60 ml of 1N NaOH containing 24.0 g of 3-nitro-4-methylbenzoyl chloride is treated as described in Example 1, using a total of 240 ml of 1N NaOH. Extraction with ether and concentration of the aqueous phase in vacuo at 55° C. to 50 ml produces a solid which is filtered after standing overnight and washed copiously with absolute alcohol and ether giving 30.3 g of product.

EXAMPLE 14

8-(4-Nitro-m-toluamido)-1,3,6-naphthalenetrisulfonic acid, trisodium salt

A 25.6 g portion of 8-amino-1,3,6-naphthalenetrisulfonic acid, trisodium salt in 100 ml of water and 60 ml of 1N NaOH containing 24.0 g of 3-methyl-4-nitrobenzoyl chloride is treated as described in Example 13. Concentration of the aqueous phase to 50 ml gives a solid non-filterable cake after cooling to room temperature. The cake is diluted with 30 ml of water, redissolved on a steam bath and allowed to stand at room temperature overnight. Filtration and copious washing with absolute alcohol and ether gives 25.22 g of the product.

EXAMPLE 15

8-(3-Amino-p-toluamido)-1,3,6-naphthalenetrisulfonic acid, trisodium salt

A 25.0 g portion of the product prepared as described in Example 13 in 100 ml of water containing 2.5 g of 10% palladium on carbon catalyst is hydrogenated at room temperature and 46 pounds pressure for 4 hours. The catalyst is filtered off. The filtrate is evaporated to a low volume, diluted with absolute alcohol filtered and washed copiously with absolute alcohol and ether giving 22.13 g of product.

EXAMPLE 16

8-(4-Amino-m-toluamido)-1,3,6-naphthalenetrisulfonic acid, trisodium salt

A 20.0 g portion of the product prepared as described in Example 14 in 100 ml of water containing 2.0 g of 10% palladium on carbon catalyst is hydrogenated at room temperature and a pressure of 46 pounds for 4 hours. The catalyst is filtered off. The filtrate is evaporated to a low volume and then diluted with absolute alcohol and triturated. The solid is filtered and washed with absolute alcohol and ether giving 18.44 g of product.

EXAMPLE 17

8,8'-[Ureylenebis(4-methyl-m-phenylenecarbonylimino)]di-1,3,6-naphthalenetrisulfonic acid, hexasodium salt A 10.0 g portion of the product prepared as described in Example 15 in 250 ml of water containing 18.5 g of anhydrous sodium carbonate is treated as described in Example 5 using a total of 37 g of sodium carbonate. The neutral solution is concentrated in vacuo at 55° C. Six successive crops of salt are removed by gradual concentration. The final crop (8.69 g) is removed by diluting with methanol, filtered while hot and the filtrate is diluted with a large volume of acetone and filtered after standing at room temperature overnight giving 7.61 g of product.

EXAMPLE 18

8,8'-[Ureylenebis(3-methyl-p-phenylenecarbonylimino)]di-1,3,6-naphthalenetrisulfonic acid, hexasodium salt A 10.0 g portion of the product prepared as described in Example 16 in 250 ml of water containing 18.5 g of anhydrous sodium carbonate is treated as described in Example 17. The neutralized reaction mixture is evaporated in vacuo at 55° C. to 150 ml which turns to a solid after cooling to room temperature overnight. Filtration and washing with 80% ethanol, absolute alcohol and ether gives 9.50 g of product.

EXAMPLE 19

8-{3-[3-(3-Nitro-p-tolyl)ureido]-p-toluamido}-1,3,6-naphthalenetrisulfonic acid, trisodium salt A 5.0 g portion of the product prepared as described in Example 15 in 75 ml of water containing 5.0 g of 4-methyl-3-nitrophenyl isocyanate is stirred vigorously at room temperature for 6 hours. The mixture is then heated to 100° C. and diluted with water. The mixture is filtered through celite and washed with water. The filtrate is salted with 50 g of sodium acetate trihydrate while warming on a steam bath. After standing overnight at room temperature the solid is broken up with a glass rod and filtered. The solid is boiled in 250 ml of absolute alcohol. Cooling in an ice bath produces a solid which is filtered and washed copiously with absolute alcohol and then with two 150 ml portions of ether giving 4.61 g of product.

EXAMPLE 20

8-{m-[3-(3-Nitro-p-tolyl)ureido]benzamido}-1,3,6-naphthalentrisulfonic acid, trisodium salt A 5.0 g portion of the product prepared as described in Example 3 in 75 ml of water containing 5.0 g of 4-methyl-3-nitrophenyl isocyanate is treated as described in Example 19 resulting in 4.62 g of product.

EXAMPLE 21

8-(5-Nitro-o-toluamido)-1,3,6-naphthalenetrisulfonic acid, trisodium salt

A 25.6 g portion of 8-amino-1,3,6-naphthalenetrisulfonic acid, trisodium salt, 100 ml of water, 60 ml of 1N NaOH and 24.0 g of 2-methyl-5-nitrobenzoyl chloride is reacted as described in Example 1, using a total of 240 ml of 1N NaOH, giving 20.48 g of product.

EXAMPLE 22

8-(5-Amino-o-toluamido)-1,3,6-naphthalenetrisulfonic acid, trisodium salt

A 23.8 g portion of the product prepared as described in Example 21 in 150 ml of water containing 2.5 g of 10% palladium on carbon catalyst is hydrogenated at room temperature and 46 pounds pressure for 3½ hours. The catalyst is filtered off. The filtrate is evaporated to a low volume, diluted with a large amount of absolute alcohol and allowed to stand at room temperature overnight. Filtration and washing with absolute alcohol and ether gives 21.5 g of product.

EXAMPLE 23

8,8'-[Ureylenebis(6-methyl-m-phenylenecarbonylimino)]di-1,3,6-naphthalenetrisulfonic acid, hexasodium salt A 10.0 g portion of the product prepared as described in Example 22 in 250 ml of water containing 18.5 g of anhydrous sodium carbonate is treated as described in Example 5. The neutral solution is concentrated in vacuo at 55° C. until precipitation occurs. The precipitate is filtered and washed with absolute alcohol. The filtrate is further concentrated to a second precipitate which is filtered and washed with absolute alcohol. The filtrate is further evaporated to a third precipitate, then diluted with 30 ml of water and heated on a steam bath. After standing overnight at room temperature the mixture is filtered and washed with absolute alcohol and ether giving 4.21 g of product.

EXAMPLE 24

8-{p-[3-(α,α,α-Trifluoro-m-tolyl)ureido]benzamido}-1,3,6-naphthalenetrisulfonic acid, trisodium salt A 3.0 g portion of the product prepared as described in Example 10 in 40 ml of water containing 3.0 ml of 3-trifloromethylphenyl isocyanate is stirred vigorously for 6 hours and treated as described in Example 19. The final volume of filtrate is salted with 20 g of sodium acetate trihydrate and allowed to stand at room temperature overnight. An additional 17.5 g of sodium acetate trihydrate is added with warming and the mixture is refrigerated. Dilution with 400 ml of absolute alcohol produces a gel which is filtered, boiled with 200 ml of absolute alcohol and filtered giving 2.94 g of product.

EXAMPLE 25

8,8'-{Oxalylbis{{[imino(4-methyl-1,3-phenylene)]-carbonyl}imino}}di-1,3,6-naphthalenetrisulfonic acid, hexasodium salt A 51.2 g portion of 8-amino-1,3,6-naphthalenetrisulfonic acid, trisodium salt, 200 ml of water, 120 ml of 1N NaOH and 26.4 g of 3-nitro-4-methylbenzoyl chloride are reacted as described in Example 1 using a total of 360 ml of 1N NaOH. The neutralized aqueous phase is concentrated to about 100 ml and filtered after standing overnight at room temperature. The resulting thick paste is filtered with the aid of 100 ml of saturated saline and washed with 100 ml of saturated saline, absolute alcohol and ether giving 55.6 g of 8-(3-nitro-4-methylbenzamido)-1,3,6-naphthalenetrisulfonic acid, trisodium salt.

The above product in 200 ml of water containing 5.5 g of 10% palladium on carbon catalyst is hydrogenated at room temperature and 46 pounds pressure for 6½ hours. The catalyst is filtered off. The filtrate is evaporated to a low volume and diluted with a large volume of absolute alcohol. Filtration and washing with 100 ml of 80% ethanol, two 100 ml portions of absolute alcohol and then ether gives a solid which is dissolved in 150 ml of water, heated on a steam bath and diluted with 600 ml of absolute alcohol. After standing overnight at room temperature the mixture is filtered and washed with absolute alcohol and ether giving 38.44 g of 8-(3-amino-4-methylbenzamido)-1,3,6-naphthalenetrisulfonic acid, trisodium salt.

A 5.0 g portion of this amino derivative, 400 ml of hexamethylphosphoramide, 1.4 ml of pyridine, 0.73 ml of oxalyl chloride and 20 ml of toluene is reacted by mixing and heating everything except the oxalyl chloride on a steam bath for 30 minutes and then cooled in an ice bath. The oxalyl chloride is added dropwise over a 50 minute period with magnetic stirring. Stirring is continued at room temperature for one hour and then filtered. A 5 ml portion of water is added to the filtrate and it is heated on a steam bath for 10 minutes. The mixture is evaporated in vacuo on a steam bath. A 250 ml portion of absolute alcohol is added to the residue and triturated. The mixture is stirred overnight at room temperature, filtered and washed with absolute alcohol and ether. The solid is dissolved in 50 ml of hot water and filtered. The filtrate is diluted with 125 ml of absolute alcohol while heating on a steam bath. The mixture is filtered and washed with absolute alcohol and ether. The filtrate is diluted with additional absolute alcohol and then filtered and washed with absolute alcohol and ether giving 1.87 g of product.

EXAMPLE 26

| Preparation of Compressed Tablet | |
|---|---|
| Ingredient | mg/Tablet |
| Active Ingredient | 0.5–500 |
| Dibasuc Calcium Phosphate NF | qs |
| Starch USP | 40 |
| Modified Starch | 10 |
| Magnesium Stearate USP | 1–5 |

EXAMPLE 27

| Preparation of Compressed Tablet-Sustained Action | |
|---|---|
| Ingredient | mg/Tablet |
| Active Ingredient as Aluminum Lake*, Micronized | 0.5–500 as acid equivalent |
| Dibasic Calcium Phosphate NF | qs |
| Alginic Acid | 20 |
| Starch | 35 |
| Magnesium Stearate USP | 1–10 |

*Complement inhibitor as sodium salt plus aluminum sulfate yields aluminum complement inhibitor plus sodium sulfate. Complements inhibitor content in aluminum lake ranges from 5–30%.

EXAMPLE 28

| Preparation of Hard Shell Capsule | |
|---|---|
| Ingredient | mg/Tablet |
| Active Ingredient | 0.5–500 |
| Lactose, Spray Dried | qs |
| Magnesium Stearate | 1–10 |

EXAMPLE 29

Preparation of Oral Liquid (Surup)

| Ingredient | % W/V |
|---|---|
| Active Ingredient | 0.05–5 |
| Liquid Sugar | 75.0 |
| Methyl Paraben USP | 0.18 |
| Propyl Paraben USP | 0.02 |
| Favoring Agent | qs |
| Purifield Water qs ad | 100.0 |

EXAMPLE 30

Preparation of Oral Liquid (Elixir)

| Ingredient | % W/V |
|---|---|
| Active Ingredients | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 31

| Ingredient | % W/V |
|---|---|
| Active Ingredient as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 32

Preparation of Injectable Solution

| Ingredient | % W/V |
|---|---|
| Active Ingredient | 0.05–5 |
| Benzyl Alcohol N.F. | 0.9 |
| Water for Injection qs ad | 100.0 |

EXAMPLE 33

Preparation of Injectable Oil

| Ingredient | % W/V |
|---|---|
| Active Ingredient | 0.05–5 |
| Benzyl Alcohol | 1.5 |
| Sesame Oil qs ad | 100.0 |

EXAMPLE 34

Preparation of Injectable Depo-Suspension

| Ingredient | % W/V |
|---|---|
| Active Ingredient as Aluminum Lake, Micronized | 0.05–5 (acid equivalent) |
| Polysorbate 80 USP | 0.2 |
| Polyethylene Glycol 4000 USP | 3.0 |

-continued

Preparation of Injectable Depo-Suspension

| Ingredient | % W/V |
|---|---|
| Sodium Chloride USP | 0.8 |
| Benzyl Alcohol N.F. | 0.9 |
| HCl to pH 6–8 | qs |
| Water for Injection qs ad | 100.0 |

EXAMPLE 35

Intra-Articular Preparation

| Ingredient | Amount |
|---|---|
| Active Ingredient (Micronized) | 2–20 mg |
| NaCl (Physiological Saline) | 0.9% |
| Benzyl Alcohol | 0.9% |
| Sodium Carboxymethylcellulose | 1–5% |
| pH adjusted to 5.0–7.5 | |
| Water for Injection qs to | 100% |

The compounds of this invention may be administered internally, e.g., orally or parenterally, such as intra-articularly, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day or every six hours for more rapidly excreted compounds may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the compound can contain from about 0.5 mg to about 500 mg.

In therapeutic use the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as nontoxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form as described herein refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers cachets, teaspoonfuls, dropperfuls, ampules, vials, segregated multiples of any of the foregoing and other forms as herein described.

The complement inhibiting activity of representative compounds of this invention has been demonstrated by one or more of the following identified tests: (i) Test, Code 026 (C1 inhibitor). This test measures the ability of activated human C1 to destroy fluid phase human C2 in the presence of C4 and appropriate dilutions of the test compound. An active inhibitor protects C2 from C1 and C4; (ii) Test, Code 035 (C3-C9 inhibitor) - This test determines the ability of the late components of human complement (C3-C9) to lyse EAC 142 in the presence of appropriate dilutions of the test compound. An active inhibitor protects EAC 142 from lysis by human C3-C9; (iii) Test, Code 036 (C-Shunt inhibitor) - In this test human erythrocytes rendered fragile are lysed in autologous serum via the shunt pathway activted by cobra venom factor in the presence of appropriate dilutions of the test compound. Inhibition of the shunt pathway results in failure of lysis; (iv) Forssman Vasculitis Test - Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/kg is then reported, unless otherwise stated; (v) Forssman Shock Test - Lethal shock is produced in guinea pigs by an i.v. injection of anti-Forssman antiserum and the harmonic mean death time of treated guinea pigs is compared with that of simultaneous controls; (vi) Complement Level Reduction Test - In this test, the above dosed guinea pigs, or others, are bled for serum and the complement level is determined in undiluted serum by the capillary tube method of U.S. Pat. No. 3,876,376 and compared to undosed control guinea pigs; and (vii) Cap 50 Test - Here, appropriate amounts of the test compound are added to a pool of guinea pig serum in vitro, after which the undiluted serum capillary tube assay referred to above is run. The concentration of compound inhibiting 50% is reported.

Table I records the results of tests, codes 026, 035, 036, Forssman shock and percent reduction of complement. Table I shows that representative compounds of the invention possess complement inhibiting activity.

TABLE I

| | Biological Activities | | | | |
|---|---|---|---|---|---|
| Compound | Code 026* | Code 035 | Code 036 | Forssman Shock*** | Percent Reduction of Complement |
| 8-p-Nitrobenzamido-1,3,6-naphthalenetrisulfonic acid, trisodium salt | +1** | | | 13 | +2 |
| 8-(p-Aminobenzamido)-1,3,6-naphthalenetrisulfonic acid, trisodium salt | +3 | | | 10 | +12 |
| 8-(4-Nitro-m-toluamido-1,3,6-naphthalenetrisulfonic acid, trisodium salt | +1 | | | 46 | +17 |
| 8-(4-Amino-m-toluamido)-1,3,6-naphthalenetrisulfonic acid, trisodium salt | +3 | | | 14 | +14 |
| 8-[m-(m-Nitrobenzamido)benzamido]-1,3,6-naphthalenetrisulfonic acid, trisodium salt | +1 | | | | |
| 8-[m-(m-Aminobenzamido)benzamido]-1,3,6-naphthalenetrisulfonic acid, trisodium salt | +2 | | | | |
| 8-{m-[3-(3-Nitro-p-tolyl)ureido]benzamido}-1,3,6-naphthalenetrisulfonic acid, trisodium salt | +2 | | | 32 | +33 |
| 8-(3-Nitro-p-toluamido)-1,3,6-naphthalenetrisulfonic acid, trisodium salt | +2 | | | 25 | −15 |
| 8-(3-Amino-p-toluamido)-1,3,6-naphthalenetrisulfonic acid, trisodium salt | +3 | | | 14 | +14 |
| 8-(5-Amino-o-toluamido)-1,3,6-naphthalenetrisulfonic acid, trisodium salt | | | | 14 | +10 |
| 8,8'-[Ureylenebis(p-phenylenecarbonylimino)]di-1,3,6-naphthalenetrisulfonic acid, hexasodium salt | +4 | | | | |
| 8,8'-[Ureylenebis(3-methyl-p-phenylenecarbonylimino)]di-1,3,6-naphthalenetrisulfonic acid, hexasodium salt | +8 +6 | | | | |
| 8,8'-[Ureylenebis(m-phenylenecarbonylimino)]di- | | | | | |

TABLE I-continued

Biological Activities

| Compound | Code 026* | Code 035 | Code 036 | Forssman Shock*** | Percent Reduction of Complement |
|---|---|---|---|---|---|
| -1,3,6-naphthalenetrisulfonic acid, hexasodium salt | +6 | | +1 | | |
| 8,8'-[Ureylenebis(4-methyl-m-phenylenecarbonylimino)]di-1,3,6-naphthalenetrisulfonic acid, hexasodium salt | +8 +6 | | | 28(i.p.) 46(i.v.) | +1 −46 |
| 8,8'-[Ureylenebis(6-methyl-m-phenylenecarbonylimino)]di-1,3,6-naphthalenetrisulfonic acid, hexasodium salt | +5 | +4 | | 11 | +2 |
| 7-m-Nitrobenzamido-1,3,6-naphthalenetrisulfonic acid, trisodium salt | | | | 20 | +14 |
| 7-(m-Aminobenzamido)-1,3,6-naphthalenetrisulfonci acid, trisodium salt | | | | 23 | +11 |
| 7,7'-[Ureylenebis(m-phenylenecarbonylimino)]di--1,3,6-naphthalenetrisulfonic acid, hexasodium salt | | +1 | +1 | 14 | −42 |
| 8,8'-{Oxalylbis{{[imino(4-methyl-1,3-phenylene)]-carbonyl}imino}}di-1,3,6-naphthalenetrisul-fonic acid, hexasodium salt | +4 | | +3 | | |
| 8,8'-{Ureylenebis[(4-methyl-m-phenylene)ureylene]}-di-1,3,6-naphthalenetrisulfonic acid, hexasodium salt | +4 | | +1 | | |

*Tests identified by code herein.
**Numbers represent activity in wells, a serial dilutions assay, higher well number indicates higher activity. The serial dilutions are two-fold.
***Harmonic mean death time in minutes. (control = 3.15 minutes).

We claim:

1. A method of inhibiting the complement system in a body fluid which comprises subjecting said body fluid to the action of an effective complement inhibiting amount of a compound of the formula:

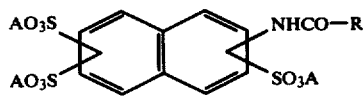

wherein R is

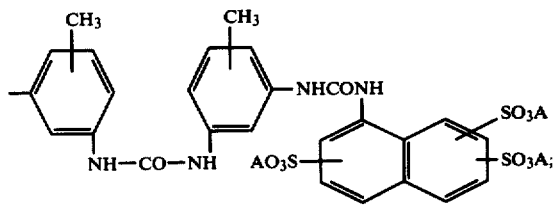

and A is hydrogen, alkali metal or alkaline earth, with the proviso that each A is identical in the same compound.

2. A method of inhibiting the complement system in a body fluid which comprises subjecting said body fluid to the action of an effective complement inhibiting amount of a compound of the formula:

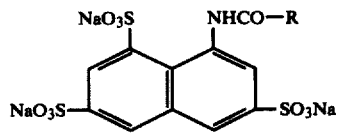

wherein R is

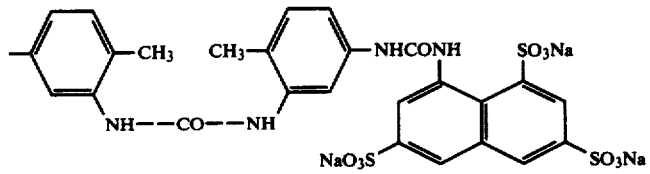

3. A method according to claim 2 wherein the compound is 8,8'-{ureylenebis[(4-methyl-m-phenylene)ureylene]}di-1,3,6-naphthalenetrisulfonic acid, hexasodium salt.

4. A method of inhibiting the complement system in a warm-blooded animal which comprises internally administering to said animal an effective complement inhibiting amount of a pharmaceutically acceptable compound of the formula:

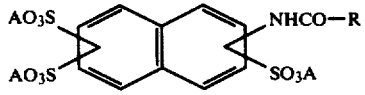

wherein R is

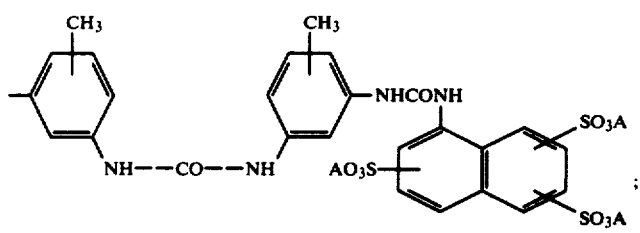

and A is hydrogen, alkali metal or alkaline earth, with the proviso that each A is identical in the same compound.

5. A method of inhibiting the complement system in a warm-blooded animal which comprises internally administering to said animal an effective complement inhibiting amount of a pharmaceutically acceptable compound of the formulae:

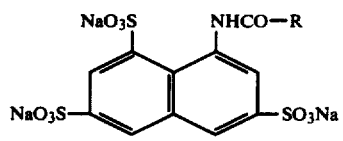

wherein R is

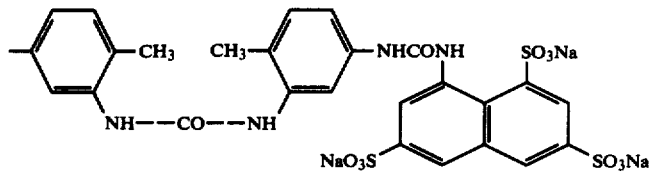

6. A method according to claim 5 wherein the compound is 8,8'-{ureylenebis[(4-methyl-m-phenylene)ureylene]}di-1,3,6-naphthalenetrisulfonic acid, hexasodium salt.

7. A method according to claim 5 wherein the compound is administered intra-articularly.